US007393365B2

(12) United States Patent
Bureiko et al.

(10) Patent No.: US 7,393,365 B2
(45) Date of Patent: Jul. 1, 2008

(54) PROCESS AND KIT-OF-PARTS FOR IMPROVED HAIR CONDITIONING AFTER COLORING BLEACHING OR PERMING

(75) Inventors: Andrei Sergeevich Bureiko, Ascot (GB); Simon Paul Godfrey, Uxbridge (GB); Olivier Charles Raineau, Paris (FR)

(73) Assignee: The Procter & Gamble Company, Cincinnati, OH (US)

( * ) Notice: Subject to any disclaimer, the term of this patent is extended or adjusted under 35 U.S.C. 154(b) by 314 days.

(21) Appl. No.: 11/116,906

(22) Filed: Apr. 28, 2005

(65) Prior Publication Data

US 2005/0241076 A1 Nov. 3, 2005

(30) Foreign Application Priority Data

Apr. 30, 2004 (EP) .................. 04252547

(51) Int. Cl.
  *D06L 3/00* (2006.01)
  *A45D 8/00* (2006.01)
  *A61K 8/00* (2006.01)
(52) U.S. Cl. ............ 8/101; 8/552; 8/554; 8/581; 132/221; 424/70.1
(58) Field of Classification Search .......... 8/405, 8/506, 552, 554, 581, 101; 132/221; 424/70.1
See application file for complete search history.

(56) References Cited

U.S. PATENT DOCUMENTS

| 4,450,152 A | 5/1984 | Ona |
| 4,620,878 A | 11/1986 | Gee |
| 4,770,873 A | 9/1988 | Wolfram |
| 5,290,545 A | 3/1994 | Halloran |
| 5,660,819 A | 8/1997 | Tsubaki |
| 5,942,216 A | 8/1999 | Herb |
| 5,981,681 A | 11/1999 | Czech |
| 6,153,570 A | 11/2000 | Decoster |
| 6,572,665 B2 * | 6/2003 | Lim et al. .......... 8/405 |
| 6,956,020 B2 | 10/2005 | Kvita |
| 6,986,886 B2 | 1/2006 | Hammond |
| 2001/0008917 A1 | 7/2001 | Craig |
| 2001/0023515 A1 | 9/2001 | Cottard |
| 2002/0120989 A1 | 9/2002 | Gomes |
| 2002/0141282 A1 | 10/2002 | Tanaka |
| 2003/0113286 A1 * | 6/2003 | Geary et al. ........ 424/70.12 |
| 2003/0115685 A1 | 6/2003 | Devin-Baudoin |
| 2003/0141489 A1 | 7/2003 | Yamada |
| 2003/0152534 A1 * | 8/2003 | Legrand et al. .......... 424/61 |
| 2003/0206879 A1 | 11/2003 | Glenn |
| 2003/0216267 A1 | 11/2003 | Snyder |
| 2004/0123402 A1 | 7/2004 | Marsh |
| 2004/0131577 A1 | 7/2004 | Davies |
| 2004/0154108 A1 | 8/2004 | Narasimhan |

FOREIGN PATENT DOCUMENTS

| EP | 0275707 A2 | 7/1988 |
| EP | 1356800 A2 | 10/2003 |
| EP | 1358865 A2 | 11/2003 |
| JP | 63051315 | 4/1988 |
| JP | 07053330 A | 2/1995 |
| JP | 07053331 A | 2/1995 |
| JP | 10306013 A | 11/1998 |
| JP | 11193223 A | 7/1999 |
| JP | 11240822 A | 9/1999 |
| JP | 2001163733 A | 6/2001 |
| JP | 2002-308723 | 10/2002 |
| WO | WO-99/49836 A1 | 10/1999 |

OTHER PUBLICATIONS

STIC Search Report dated Apr. 4, 2007.*
XP002303490, "Clear Conditioning Shampoo", *Happi Formulary*, Oct. 2001, www.happi.com/special/1001form.htm.
Xp002303491, M. Schlossman Ed., "The Chemistry and Manufacture of Cosmetics: Formulating", vol. II, 3rd ed., 2000, p. 426-428, Allured Pub., US 277870.
"Dow Corning 8813 Polymer", Online!, Aug. 16, 1999, pp. 1, XP002258822.
"Dow Corning 2-8040 Polymer", Online!, Oct. 1, 1999, pp. 1, XP00225821.
"Dow Corning 2-8822A Polymer Silicone Softener", Online!, Oct. 1, 1999, XP002258823.
"Dow Corning 8803 Softener", Online!, Jan. 4, 2001, XP002258244.
"Wacker-Belsil ADM 652, ADM 656, ADM 1100, ADM 1600, ADM 1650", Online!, Jan. 2000, XP002258243.

* cited by examiner

*Primary Examiner*—Eisa B Elhilo
(74) *Attorney, Agent, or Firm*—Melissa G. Krasovec

(57) ABSTRACT

The present invention relates to the field of hair care. More specifically, the present invention relates to the conditioning of hair after it has been oxidised in a coloring, bleaching or perming treatment. Superior conditioning is obtained by providing a cationic polymer to the hair while it is subjected to the oxidising treatment, and then the oxidised hair is subjected to a conditioning treatment with a composition comprising a functionalized silicone.

2 Claims, No Drawings

PROCESS AND KIT-OF-PARTS FOR IMPROVED HAIR CONDITIONING AFTER COLORING BLEACHING OR PERMING

FIELD OF THE INVENTION

The present invention relates to the field of hair care. More specifically, the present invention relates to the conditioning of hair after it has been colored or permed.

BACKGROUND OF THE INVENTION

Oxidizing compositions, for example those designed for hair bleaching or decolouration, permanent coloring, or permanently reshaping of hair, lead to irreversible physico-chemical changes to the hair. These irreversible physico-chemical changes can manifest themselves as increased roughness, brittleness and dryness leading to less manageable hair. The use of conditioners within the coloring, bleaching or penning process is known. Conditioning materials can be added to the colorant or perming product, or alternatively these can be supplied within the colorant or perming kit as a separate conditioner, and can thereby be applied to the hair either during the coloring or perming event or after rinsing. As described in EP 0 275 707, it is known to use aminosilicones for this purpose. However, it has also been established that, in the case of more polar hair, such as that obtained after successive oxidation events, aminosilicone deposition is greatly reduced and cannot provide the same level of benefit in hair condition. Without wishing to be bound by theory, the reason for this may be that there exists a surface energy incompatibility between the polar chemically damaged hair with the relatively non-polar aminosilicone leading to poorer adhesion.

Conditioning composition comprising a functionalized silicone conditioning agent which deposits evenly on all types of hair which occur in today's human population, from undamaged, virgin hair, at the one extreme, to hair exposed to multiple oxidative dye treatments, at the other, go some way to improving the conditioning effect of hair treated with an oxidizing composition, both in the short and long term after application. Such compositions have been described in EP 1 358 865 and EP 1 356 800, however, even these do not deliver an optimal conditioning effect to the hair over the interval from application, through to repeated washing cycles.

Summarising, it is an object of the present invention to produce from an oxidizing treatment system, a superior conditioner that deposits evenly and durably on hair of differing damage states, from undamaged, virgin hair, at the one extreme, to hair exposed to multiple oxidative treatments, at the other, and which does not wash off so rapidly that the conditioning benefit is lost to the consumer.

In response, we have found that superior conditioning could be obtained by providing a cationic polymer to the hair while it is subjected to the oxidising treatment, and then providing to said oxidised hair a functionalized silicone. The combination of these two subsequent treatments delivers a greater conditioned feel than either when used as a standalone conditioning treatment. The two conditioning systems synergise to deliver a superior level of conditioning immediately after and during the early stages of washing post oxidizing treatment, while still retaining the long term conditioning benefits. This cannot be achieved by using the silicone alone, without causing a trade off in so-called "clean-feel" attributes.

SUMMARY OF THE INVENTION

In a first embodiment, the present invention encompasses a process for the treatment of hair, wherein said hair is subjected to an oxidising treatment in the presence of a cationic polymer, and said oxidised hair is then provided with a functionalized silicone.

In a second embodiment, the present invention encompasses a kit-of-parts for the treatment of hair which comprises a composition comprising an oxidising agent, a composition comprising a cationic polymer to be used in a step where said hair is oxidised, and a composition which comprises a functionalized silicone which is to be used in a step subsequent to said oxidizing step.

DETAILED DESCRIPTION OF THE INVENTION

The present invention involves the use of two cosmetically acceptable compositions for treating human hair. The first is an oxidising composition containing an oxidizing agent, which can either be a coloring, decoloring, bleaching, or perming composition. According to the invention, this composition containing an oxidising agent also comprises, in use, a cationic polymer. The second composition is a conditioning composition comprising a functional silicone polymer having an interfacial tension (IFT) between 1 and 12 mN/m and a viscosity from 400 to 150,000 cps, wherein the silicone deposits durably onto hair.

The Oxidising Composition

Oxidizing agents for use herein can be inorganic or organic oxidising agents. The oxidising agent is preferably present in the composition at a level of from about 0.01% to about 20%, preferably from about 0.01% to about 14%, more preferably from about 0.5% to about 12% by weight of the composition.

The inorganic peroxygen oxidising agents useful herein are generally inorganic peroxygen materials capable of yielding peroxide in an aqueous solution. The inorganic peroxygen oxidising agent should be safe and effective for use in the present compositions. Preferably, the inorganic peroxygen oxidising agents suitable for use herein will be soluble in the compositions according to the present invention when in liquid form or in the form intended to be used. Preferably, inorganic peroxygen oxidising agents suitable for use herein will be water-soluble. Water-soluble oxidising agents as defined herein mean agents, which have a solubility to the extent of about 10 g in 1000 ml of deionised water at 25° C. ("Chemistry" C. E. Mortimer. 5th Edn. p277).

Inorganic peroxygen oxidising agents are well known in the art and include hydrogen peroxide, inorganic alkali metal peroxides such as sodium periodate, sodium perbromate and sodium peroxide, and inorganic perhydrate salt oxidising compounds, such as the alkali metal salts of perborates, percarbonates, perphosphates, persilicates, persulphates and the like. These inorganic perhydrate salts may be incorporated as monohydrates, tetrahydrates etc. Mixtures of two or more of such inorganic peroxygen oxidising agents can be used if desired. While alkali metal bromates and iodates are suitable for use herein, the bromates are preferred. Highly preferred for use in the compositions according to the present invention is hydrogen peroxide.

The compositions herein may instead or in addition to the inorganic peroxygen oxidising agent(s), comprise one or more preformed organic peroxyacid oxidising agents.

Suitable organic peroxyacid oxidising agents for use in the coloring compositions according to the present invention have the general formula:

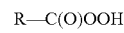

wherein R is selected from saturated or unsaturated, substituted or unsubstituted, straight or branched chain, alkyl, aryl or alkaryl groups with from 1 to 14 carbon atoms.

The organic peroxyacid oxidising agents should be safe and effective for use in the compositions herein. Preferably, the preformed organic peroxyacid oxidising agents suitable for use herein will be soluble in the compositions used according to the present invention when in liquid form and in the form intended to be used. Preferably, organic peroxyacid oxidising agents suitable for use herein will be water-soluble. Water-soluble preformed organic peroxyacid oxidising agents as defined herein means agents, which have solubility to the extent of about 10 g in 1000 ml of deionised water at 25° C. ("Chemistry" C. E. Mortimer. 5th Edn. p277).

The oxidizing compositions can be, for example, aqueous, and the pH of the aqueous oxidising composition may be in the range, for example, from 1 to 13, more preferably between 2 and 12.

The oxidizing composition may also, as in the case of hair bleaching or colouring, be in the form of two parts to be mixed together at the time of use prior to use, one of these two parts comprising alkaline agents and being in a solid or liquid form. For the hydrogen peroxide component, the pH can be below 7 before mixing.

The pH of the aqueous oxidising compositions may be obtained and/or adjusted conventionally either by adding basifying agents, alone or as a mixture, such as aqueous ammonia, monoethanolamine, diethanolamine, triethanolamine, isopropanolamine, 1,3-propanediamine, an alkali metal or ammonium carbonate and bicarbonate, an organic carbonate such as guanidine carbonate, an alkali metal hydroxide, or by adding acidifying agents, alone or as a mixture, such as hydrochloric acid, acetic acid, lactic acid and boric acid.

The compositions herein may optionally contain a transition metal containing catalyst for the inorganic peroxygen oxidising agents and the optional preformed peroxy acid oxidising agent(s). Suitable catalysts for use herein are disclosed in WO98/27945.

The compositions herein may contain as an optional component a heavy metal ion sequestrant. By heavy metal ion sequestrant it is meant herein components, which act to sequester (chelate or scavenge) heavy metal ions. These components may also have calcium and magnesium chelation capacity, but preferably they show selectivity to binding heavy metal ions such as iron, manganese and copper. Such sequestering agents are valuable in hair coloring compositions as herein described for the delivery of controlled oxidising action as well as for the provision of good storage stability of the hair coloring products.

Heavy metal ion sequestrants may be present at a level of from about 0.005% to about 20%, preferably from about 0.01% to about 10%, more preferably from about 0.05% to about 2% by weight of the compositions.

For bleaching or decolouring keratin fibres, the oxidising composition can be in the form of a single product which applied directly onto the keratin fibres and left for a period of time ranging from a few seconds, up to days, before optionally rinsing with water. Alternatively the oxidizing composition can be in the form of two products that are mixed before applying to the keratin fibres, this mixed composition is typically left on the hair from a few seconds to several hours, before optionally rinsing, more preferable from 1 to 50 minutes, before optionally rinsing. Alternatively, the oxidizing composition can be in the form of three products that are mixed before applying to the keratin fibres, this mixed composition is typically left on the hair from a few seconds to several hours, before optionally rinsing, more preferable from 1 to 50 minutes, before optionally rinsing. Compositions which contain further components which are applied to the hair at the same time as the oxidizing component are also included within the present invention.

Oxidizing compositions can further be used to dye or colour keratin fibres, using so-called oxidation dyeing or colouring, which employs oxidation dye precursors together with the oxidizing agent, which may impart to the keratin fibres a colour which is long lasting.

The concentration of each oxidative hair-coloring agent in the compositions according to the present invention may be from about 0.0001% to about 5% by weight.

Any oxidative hair-coloring agent can be used in the compositions herein. Typically, oxidative hair coloring agents comprise at least two components, which are collectively referred to as dye forming intermediates (or precursors). Dye forming intermediates can react in the presence of a suitable oxidant to form a colored molecule.

The dye forming intermediates used in oxidative hair colorants include: aromatic diamines, aminophenols, various heterocycles, phenols, napthols and their various derivatives. These dye forming intermediates can be broadly classified as; primary intermediates and secondary intermediates. Primary intermediates, which are also known as oxidative dye precursors, are chemical compounds which become activated upon oxidation and can then react with each other and/or with couplers to form colored dye complexes. The secondary intermediates, also known as color modifiers or couplers, are generally colorless molecules which can form colors in the presence of activated precursors/primary intermediates, and are used with other intermediates to generate specific color effects or to stabilise the color.

Primary intermediates suitable for use in the compositions and processes herein include: aromatic diamines, polyhydric phenols, amino phenols and derivatives of these aromatic compounds (e.g., N-substituted derivatives of the amines, and ethers of the phenols). Such primary intermediates are generally colorless molecules prior to oxidation.

While not wishing to be bound by any particular theory, it is believed that the process by which color is generated from these primary intermediates and secondary coupler compounds generally includes a stepwise sequence whereby the primary intermediate can become activated (by oxidation), and then enjoins with a coupler to give a dimeric, conjugated colored species, which in turn can enjoin with another 'activated' primary intermediate to produce a trimeric conjugated colored molecule.

In general terms, oxidative dye primary intermediates include those materials which, on oxidation, form oligomers or polymers having extended conjugated systems of electrons in their molecular structure. Because of the new electronic structure, the resultant oligomers and polymers exhibit a shift in their electronic spectra to the visible range and appear colored. For example, oxidative primary intermediates capable of forming colored polymers include materials such as aniline, which has a single functional group and which, on oxidation, forms a series of conjugated imines and quinoid dimers, trimers, etc. ranging in color from green to black. Compounds such as p-phenylenediamine, which has two functional groups, are capable of oxidative polymerization to yield higher molecular weight colored materials having extended conjugated electron systems. Oxidative dyes known in the art can be used in the compositions according to the present invention. A representative list of primary intermediates and secondary couplers suitable for use herein is found in Sagarin, "Cosmetic Science and Technology","Interscience, Special Ed. Vol. 2 pages 308 to 310.

The primary intermediates can be used alone or in combination with other primary intermediates, and one or more can be used in combination with one or more couplers. The choice of primary intermediates and couplers will be determined by the color, shade and intensity of coloration which is desired. There are nineteen preferred primary intermediates and couplers which can be used herein, singly or in combination, to provide dyes having a variety of shades ranging from ash blonde to black; these are: pyrogallol, resorcinol, p-toluenediamine, p-phenylenediamine, o-phenylenediamine, m-phenylenediamine, o-aminophenol, p-aminophenol, 4-amino-2-nitrophenol, nitro-p-phenylenediamine, N-phenyl-p-phenylenediamine, m-aminophenol, 2-amino-3-hydroxypyridine, 1-napthol, N,N bis (2-hydroxyethyl)$_p$-phenylenediamine, resourcinol, diaminopyrazole, 4-amino-2-hydroxytoluene, 1,5-dihydroxynapthalene, 2-methyl resorcinol and 2,4-diaminoanisole. These can be used in the molecular form or in the form of peroxide-compatible salts.

The hair coloring compositions of the present invention may, in addition to or instead of an oxidative hair coloring agent, include non-oxidative and other dye materials. Optional non-oxidative and other dyes suitable for use in the hair coloring compositions and processes according to the present invention include both semi-permanent, temporary and other dyes. Non-oxidative dyes as defined herein include the so-called 'direct action dyes', metallic dyes, metal chelate dyes, fiber reactive dyes and other synthetic and natural dyes. Various types of non-oxidative dyes are detailed in: 'Chemical and Physical Behaviour of Human Hair' 3rd Ed. by Clarence Robbins (pp250-259); 'The Chemistry and Manufacture of Cosmetics'. Volume IV. 2nd Ed. Maison G. De Navarre at chapter 45 by G. S. Kass (pp841-920); 'cosmetics: Science and Technology' 2nd Ed., Vol. II Balsam Sagarin, Chapter 23 by F. E. Wall (pp 279-343); 'The Science of Hair Care' edited by C. Zviak, Chapter 7 (pp 235-261) and .'Hair Dyes', J. C. Johnson, Noyes Data Corp., Park Ridge, U.S.A. (1973), (pp 3-91 and 113-139).

For colouring keratin fibres, the oxidising composition can be in the form of a single product which applied directly onto the keratin fibres and left for a period of time ranging from a few seconds, up to days, before optionally rinsing with water. Alternatively the oxidizing composition can be in the form of two products that are mixed before applying to the keratin fibres, this mixed composition is typically left on the hair from a few seconds to several hours, before optionally rinsing, more preferable from 1 to 50 minutes, before optionally rinsing. Alternatively the oxidizing composition can be in the form of three products that are mixed before applying to the keratin fibres, this mixed composition is typically left on the hair from a few seconds to several hours, before optionally rinsing, more preferable from 1 to 50 minutes, before optionally rinsing. Compositions, which contain further components, which are applied to the hair at the same time as the oxidizing component, are also included within the present invention.

Oxidizing compositions also find use in the process of permanently reshaping keratin fibres such as hair. During this process, a reducing composition is first applied to the hair, the hair shape is then moved as desired and the hair is left for a period of time ranging from a few seconds to 60 minutes, more preferably from 10 to 40 minutes. The hair is then optionally rinsed with water before an oxidizing composition is applied to the hair for a period of time ranging from a few seconds to 60 minutes, more preferably from 10 to 40 minutes. The Keratin fibres, such as hair are then rinsed and the hair release from the desired shape, and dried. When dry, the hair retains at least part of the desired shape. A discussion of permanently reshaping hair can be found in "Chemical and Physcial Behaviour of Human Hair" by Clarence R Robbins, Springer-Verlag, N.Y., 1994.

In this invention, the composition which contains an oxidizing agent, which can be used to bleach or decolour keratin fibres, colour keratin fibres or permanently reshape keratin fibres, also contains a cationic polymer.

Accordingly, in one embodiment of this invention there is provided a process for the treatment of hair, wherein said hair is subjected to an oxidising treatment in the presence of a cationic polymer, and said oxidised hair is then provided with a functionalized silicone. And in that embodiment, the oxidising treatment can be a coloring treatment, a bleaching treatment, or a penning treatment.

Similarly, in a second embodiment of this invention, there is provided a kit-of-parts for the treatment of hair which comprises a composition comprising an oxidising agent, a composition comprising a cationic polymer to be used in a step where said hair is oxidised, and a composition which comprises a functionalized silicone which is to be used in a step subsequent to said oxidizing step. In this second embodiment, the kit-of-parts may be a kit for the coloring of hair, and said cationic polymer is then present in a composition which further comprises a hair dye and which is suitable for the formation of a hair coloring composition. Or, the kit-of-parts could be a kit for the bleaching of hair, and said cationic polymer is then present in either the alkalising system and/or the oxidizing system which are suitable for the formation of a composition for the bleaching of hair (i.e. the composition comprising the oxidising agent is the composition comprising the cationic polymer). Or, the kit-of-parts could be a kit for the penning of hair, and said cationic polymer is then present in either a composition which comprises a hair reducing agent and/or an oxidizing composition which are suitable for use in the perming of hair.

As used herein, the expression "cationic polymer" refers to any polymer comprising cationic groups and/or groups which may be ionised into cationic groups. Conditioners of cationic polymer type may be chosen from those already know by those skilled in the art as improving at least one cosmetic properties of keratin fibres treated with a cosmetic composition. Cationic polymers can be chosen from those comprising units of at least one amine group chosen from primary, secondary, tertiary and quaternary amine groups that may either form part of the main polymer chain, or be borne by a side substituant that is directly attached to the main polymer chain. Such cationic polymers generally have a number average molecular mass ranging from 500 to $5 \times 10^6$, or more preferably from 1000 to $3 \times 10^6$. Polymers of the polyamine, polyamino amide and polyquaternary ammonium type that may be used include but are not limited to:

1) homopolymers and copolymers derived from acrylic or methacrylic esters or amides. Copolymers of these polymers can also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinylactams such as vinlypyrrolidone and vinylcaprolactam, and vinyl esters. Examples of such polymers include:
   Copolymers of acrylamide and of methacryloyloxyethyltrimethylammonium methosulfate, examples of which include polymers known via the INCI nomenclature as Polquaternium-5, such as the products sold under the names Reten 210, Reten 220, Reten 230, Reten 240, Reten 1104, Reten 1105, Reten 1006 by the company Hercules and Merquat 5, Merquat 5 SF by the company Nalco.

Copolymers of vinylpyrrolidone and dimethylaminopropyl methacrylamide, examples of which include polymers known via the INCI nomenclature as Polyquaternium-28, such as the products sold under the name Gafquat HS-100 by the company International Speciality Products (ISP).

Coplolymers of vinyl pyrrolidone and dialkyaminoalkyl acrylates or methactylates, examples of which include polymers known via the INCI nomenclature as Polquaternium-11, such as the products sold under the name Gafquat 440, Gafquat 734, Gafquat 755, Gafquat 755N by the company International Speciality Products (ISP), and Luviquat PQ11 PM by the company BASF and Polyquat-11 SL by the company Sino Lion.

Copolymers vinylpyrrolidone, dimethylaminopropyl methacrylamide and methacryloylaminopropyl lauryidimonium chloride, examples of which include polymers known via the INCI nomenclature as polyquaternium-55, such as the products sold under the name Styleze W-20 by the company International Speciality Products (ISP).

Copolymers of acrylic acid, acrylamide and methacrylamidopropyltrimonium chloride, examples of which include polymers known via the INCI nomenclature as Polyquaternium-53, such as the products sold under the name Merquat 2003 by the company Nalco.

Copolymers of dimethyaminopropylacrylate (DMAPA), acrylic acid and acrylonitrogens and diethyl sulfate, examples of which include polymers known via the INCI nomenclature as Polyquaternium-31, such as the products sold under the name Hypan QT100 by the company Lipo.

Copolymers of acrylamide, acrylamidopropyltrimonium chloride, 2-amidopropylacrylamide sulfonate, and dimethyaminopropylacrylate (DMAPA), examples of which include polymers known via the INCI nomenclature as polyquaternium-43, such as the products sold under the name Bozequat 4000 by the company Clairant.

Copolymers of acrylic acid, methylacrylate and methacrylamidopropyltrimonium chloride, examples of which include polymers known via the INCI nomenclature as Polyquaternium-47, such as the products sold under the name Merquat 2001 and Merquat 2001N sold commercially by Nalco.

Copolymes of methacryloyl ethyl betaine, 2-hydroxyethyl methacrylate and methacryloyl ethyl trimethyl ammonium chloride, examples of which include polymers known via the INCI nomenclature as Polyquaternium-48, such as the products sold under the name Plascize L-450 by the company Goo Chemcial.

Copolymers of acrylic acid diallyl dimethyl ammonium chloride and acrylamide, examples of which include polymers known via the INCI nomenclature as polyquaternium 39, such as the products sold under the name Merquat 3330 and Merquat 3331 by the company Nalco.

Further examples include copolymers of methacrylamide methacrylamidopropyltrimonium and methacryloylethyltrimethyl ammonium chloride and their derivatives, either homo or copolymerised with other monomers, examples of which include polymers known via the INCI nomenclature as: Polyquaternium-8, Polyquaternium-9, Polyquaternium-12, Polyquaternium-13 Polyquaternium-14, Polyquaternium-15, such as the products sold under the name Rohagit KF 720 F by the company Rohm, Polyquaternium-30, such as the products sold under the name Mexomere PX by the company Chimex, Polyquaternium-33, Polyquaternium-35, Polyquaternium-36, such as the products sold under the name Plex 3074 L by the company Rhon, Polyquaternium 45, such as the products sold under the name Plex 3073L by the company Rohn, Polyquaternium 49, such as the products sold under the name Plascize L-440 by the company Goo Chemicals, Polyquaternium 50 such as the products sold under the name Plascize L-441 by the company Goo Chemicals, Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Examples include but are not limited to Copolymers of hydroxyethylcelluloses and diallyldimethyl ammonium chlorides, examples of which include polymers known via the INCI nomenclature as Polyquaternium-4, such as the products sold under the name Celquat L 200 and Celquat H 100 by the company National Starch.

Copolymers of hydroxyethylcelluloses and a trimethyl ammonium substituted epoxide, examples of which include polymers known via the INCI nomenclature as Polyquaternium-10, such as the products sold under the name AEC Polyquaternium-10 by the company A&E Connock , Catinal C-100 Catinal HC-35 Catinal HC-100 Catinal HC-200 Catinal LC-100 Catinal LC-200 by the company Toho, Celquat SC-240C Celquat SC-230M, by the company National Starch, Dekaquat 400, Dekaquat 3000 by the company Dekker, Leogard GP by the company Akzo Nobel, RITA Polyquta 400 RITA, Polyquta 3000 by the company RITA, UCARE Polymer JR-125 UCARE Polymer JR-400 UCARE Polymer JR-30M UCARE Polymer LK UCARE Polymer LR 400 UCARE Polymer LR 30M by the company Amerchol.

Copolymers of hydroxyethylcelluloses and lauryl dimethyl ammonium substituted epoxides, examples of which include polymers known via the INCI nomenclature as Polyquaternium-24, such as the products sold under the name Quatrisoft polymer LM-200 by the company Amerchol.

Derivatives of Hydroxypropyl Guar, examples of which include polymers known via the INCI nomenclature as Guar Hydroxypropyltrimonium Chloride, such as the products sold under the name Catinal CG-100, Catinal CG-200 by the company Toho, Cosmedia Guar C-261N, Cosmedia Guar C-261N, Cosmedia Guar C-261N by the company Cognis, DiaGum P 5070 by the company Freedom Chemical Diamalt, N-Hance Cationic Guar by the company Hercules/Aqualon, Hi-Care 1000, Jaguar C-17, Jaguar C-2000, Jaguar C-13S, Jaguar C-14S, Jaguar Excel by the company Rhodia, Kiprogum CW, Kiprogum NGK by the company Nippon Starch.

Hydroxypropyl derivatives of Guar Hydroxypropyltrimonium Chloride, examples of which include polymers known via the INCI nomenclature as Hydroxypropyl Guar Hydroxypropyltrimonium Chloride, such as the products sold under the name Jagaur C-162 by the company Rhodia.

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.
4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Non-limiting examples of such derivatives include the adipic acid/epxoypropyl/diethylenetriamine.
5) Cyclopolymers of dialkdiallylamine or of dialkyldiallyammonium, among which polymers mention may be made of:
   Dimethyldiallyammonium chloride polymers, examples of which include polymers known via the INCI nomenclature as Polyquaternium-6, such as the products sold under the name Merquat 100 by the company Nalco, Mirapol 100 by the company Rhodia, Rheocare CC6 by the company Cosmetic Rheologies, AEC polyquaternium-6 by the company A&E Connock, Agequat 400 by the company CPS, Conditioner P6 by the company 3V Inc., Flocare C106 by the company SNF, Genamin PDAC by the company Clariant, Mackernium 006 by the company McIntyre.
   Copolymers of acrylamides and dimethyldiallylammonium chlorides monomers, examples of which include polymers known via the INCI nomenclature as Polyquaternium-7, such as the products sold under the name AEC Polyquaternium-7 by the company A&E Connock, Agequat-5008, Agequat C-505 by the company CPS, Conditioner P7 by the company 3V Inc. Flocare C 107 by the company SNF Mackernium 007, Mackernium 007S by the company McIntyre, ME Polymer 09W by the company Toho, Merquat 550, Merquat 2200, Merquat S by the company Nalco, Mirapol 550 by the company Rhodia, Rheocare CC7, Rheocare CCP7 by the company Cosmetic Rheologies, Salcare HSP-7, Salcare SC 10, Salcare Super 7 by the company Ciba.
   Copolymers of dimethyldiallylammoniumchlorides and acrylic acids, examples of which include polymers known via the INCI nomenclature as polyquaternary-22, such as the products sold under the name Merquat 280 and Merquat 295 by the company Nalco.
6) Quaternary diammonium polymers comprising repeat units corresponding to [—N+(R1)(R2)-A1-N+(R3)(R4)-B1-] [2X-], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are choen from liner or branched $C_1$-$C_6$ alkyl radicals substituted with at least one group chosen from nitrile, ester, acyl and amide groups and groups of —CO—O—R5-D and —CO—NH—R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X— is an anion derived from inorganic and organic acids. D is chosen from a glycol residue, a bis-secondary diamine residue, a bis-primary diamine residue or a ureylene group. An examples of which include polymers known via the INCI nomenclature as Hexadimethrine chloride, where R1, R2, R3 and R4 are each methyl radicals, A1 is (CH2)3 and B1 is (CH2)6 and X=Cl. examples of which include polymers known via the INCI nomenclature as polyquaternium-34 where R1and R2 are ethyl radicals and R3 and R4 are methyl radicals and A1 is (CH2)3 and B1 is (CH2)3 and X=Br, such as the products sold under the name Mexomere PAX by the company Chimax.
7) Polyquaternary ammonium polymers comprising repeating units of formula [—N+(R6)(R7)-(CH2)r-NH—CO—(CH2)q-(CO)t-NH—(CH2)s-N+(R8)(R9)-A-][2X-], in which R6, R7, R8 and R9 which may be identical or different, are chosen from a hydrogen atom and a methyl, ethyl, propyl, □-hydroxyethyl, □-hydroxypropyl, and —CH2CH2(OCH2CH2)pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X- is anion such as a halide. T is an integer chosen to be equal to 0 or 1. A is chosen from divalent radicals such as —CH2—CH2—O—CH2—CH2—.

Examples of which include
   Polymers known via the INCI nomenclature as polyquaternium-2, where r=s=3, q=0,t=0, R6, R7, R8 and R9 are methyl groups, and A is —CH2—CH2—O—CH2—CH2, such as the products sold under the name Ethpol PQ-2 from Ethox and Mirapol A-15 by the company Rhodia.
   Polymers known via the INCI nomenclature as polyquatemium-17 where r=s=3, q=4, t=1 R6, R7, R8 and R9 are methyl groups, and A is —CH2—CH2—O—CH2—CH2.
   Polymers known via the INCI nomenclature as Polyquaternium 18, where r=s=3, q=7, t=1 R6, R7, R8 and R9 are methyl groups, and A is —CH2—CH2—O—CH2—CH2
   Polymers known via the INCI nomenclature as the block copolymer formed by the reaction of Polyquaternium-2 with Polyquaternium-17, known as Polyquaternium 27, such as the products sold under the name Mirapol 175 by the company Rhodia.
8) Copolymers of vinylpyrrolidones and of vinylimidazoles and optionally vinylcaprolactums, examples of which include polymers known via the INCI nomenclature as Polyquaternary-16 formed from methylvinylimidazolium chlorides and vinylpyrrolidones, such as the products sold under the name Luviquat FC370, Luviquat FC550, Luviquat FC905, Luviquat HM-552 by the company BASF. Or copolymers of vinylcaprolactams and vinylpyrrolidones with methylvinylimidazolium methosulfates, examples of which include polymers known via the INCI nomenclature as Polyquaternium-46, such as the products sold under the name Luviquat Hold by the company BASF. Or copolymers of vinylpyrrolidones and quaternized imidazolines, examples of which include polymers known via the INCI nomenclature poylquaterary 44, such as the products sold under the name Luviquat Care by the company BASF
9) Polyamines such as the product Polyquart H sold by Cognis under the reference name polyethylene glycol (15) tallow polyamine in the CTFA dictionary.

10) Cross linked methacryloyloxy(C1-C4)alkyltri(C1-C4) alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, examples of which include polymers known via the INCI nomenclature as Polyquaternium-37, such as the products sold under the name Synthalen, CN Synthalen CR, Synthalen CU, sold by 3V sigma, or as a dispersion in another media such as the products sold under the name Salcare SC95 and Salcare SC96 by the company Ciba or Rheocare CTH(E) by the company Cosmetic Rheologies. Or in another example of which include polymers known via the INCI nomenclature as Polyquaternium-32, or when sold as a dispersion in mineral oil such as the products sold under the name Salcare SC92 by the company Ciba.

11) Further examples of cationic polymers include polymers known via the INCI nomenclature as Polyquaternium 51, such as the products sold under the name Lipidure-PMB by the company NOF, via the INCI nomenclature as Polyquaternium 54, such as the products sold under the name Qualty-Hy by the company Mitsui, and via the INCI nomenclature as Polyquaternium 56 such as the products sold under the name Hairrol UC-4 by the company Sanyo chemicals.

12) silicone polymers comprising cationic groups and/or groups which may be ionised into cationic groups. For example:

cationic silicones of the general formula (R10-N+(CH3)2) R11-(Si(CH3)2-O)x-R11-(N+(CH3)2)-R10), where R10 is an alkyl derived from coconut oil, and R11 is (CH2CHOCH2O(CH2)3 and x is a number between 20 and 2000, examples of which include polymers known by the INCI nomenclature as Quaternium 80, such as the products sold under the name as Abil Quat 3272 and Abil Quat 3474 sold commercially by Goldschmidt.

Silicones containing groups which may be ionised into cationic groups—for example aminosilicones containing at least 10 repeating siloxane —Si(CH3)2-O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3 Si—O or R12(CH3)2Si—O, where R12 can be either OH or OR13, where R13 is a C1-C8 alky group, or a mixture of both functional terminal groups. These silicones are also available as preformed emulsions. Polymer with terminal siloxane units of (CH3)3Si—O examples of which include polymers known by the INCI nomenclature as trimethylsilylamodimethicone, such as the products sold under the name as DC-2-8566, DC 7224 and DC-2-8220 sold commercially by Dow Corning and SF1708 and SM 2125 sold commercially by GE Silicones and Wacker Belsil ADM 653 sold commercially by Wacker silicones. Further examples include polymers with terminal siloxane units of (R12O)(CH3)2Si—O where R12 can be either OH or OR13, where R13 is a C1-C8 alky group, or a mixture of both functional terminal groups, known by the INCI nomenclature as amodimethicone, such as the products sold under the name as Wacker Belsil ADM 1100, Wacker Belsil ADM 1600, Wacker Belsil ADM 652, Wacker Belsil ADM 6057E, Wacker Belsil ADM 8020 sold commercial by Wacker Silicones, DC929, DC939 and DC949 sold commercially by Dow Corning and SM2059 sold commercially by GE silicones.

Silicones containing groups which may be ionised into cationic groups—for example silicones containing at least 10 repeating siloxane —Si(CH3)2—O) units within the polymer chain, with either terminal, graft or a mixture of terminal and graft aminofunctional groups, together with additional functional groups. Additional functional groups can include polyoxyalkylene, the reaction product of amines and carbinols, alky chains. For example products know by the INCI nomenclature as methoxy PEG/PPG-7/3 Aminopropyl Dimethicone, such as the product sold under the name of Abil Soft AF100 sold commercially by Degussa. For example products know by the INCI nomenclature as Bis (C13-15 Alkoxy) PG Amodimethicone, such as the product sold under the name of DC 8500 sold commercially by Dow Corning.

Those skilled in the art would be able to choose either one or a selection of the aforementioned cationic polymers so as to improve at least one cosmetic properties of keratin fibres treated with a cosmetic composition.

The oxidizing compositions can also optionally contain other actives which improving at least one cosmetic properties of keratin fibres treated with a cosmetic composition. Such actives can be selected by those skilled in the art.

The composition containing an oxidizing agent, which can either bleach or decolour keratin fibres, colour the keratin fibres or for use in the process of permanently reshaping the keratin fibres, may also comprise at least one additive chosen from thickeners, antidandruff and antiseborrhoeic agents, fragrances, nacreouse agents, hydroxy acids, electrolytes, preserving agents, sunscreens, vitamins, provitamins such as panthenol, amionic and non-ionic polymers, silicones, organofunctional silicones, proteins, protein hydrosylates, 18-methyleicosanoic acid, anionic, cationic, non-ionic, amphoteric or zwitterionic surfactants; buffers, masking fragrances, dispersing agents, stabilizers, perfumes, non-ionic polymers, anionic polymers, complex coacervates, complex coacervate capsules, metal salts, lewis acids, buffering agents, particulate thickeners, polymeric thickeners, wax thickeners, oils, emollients, humectants, moisturizers, pearlescents, opacifiers, enzymes, suspending agents, antimicrobials, preservatives, proteins, herb and plant extracts, bleach, peroxide, polyols, silicones, antibodies, pH adjusting agents including pH buffers, viscosity modifiers, preservatives, viscosity enhancers, gelling agents, chelators, oxidising agents, reducing agents, UV filters, emulsifying agents, moisturizing and conditioning agents, and other common adjuvants well known to those skilled in the art, and also mixtures of these various compounds and any other additive usually used in cosmetic compositions. These additives may be present in the composition in proportions that may range between 0 and 20% by weight relative to the total composition. The amount of each additive required can be determined by a person skilled in the art, depending on the composition's nature and its function.

The Conditioning Composition

The conditioning compositions for use herein are characterised in that they comprise a functionalised silicone. Suitable silicones for use herein are in turn best characterised by some of their physical properties. Indeed, it has been observed that silicone droplets tend to interact with strands of hair predominantly as fluids and not as individual molecules. A number of parameters were investigated and matched against the objectives. We identified that, within a certain hydrophilicity range, advantageous technical benefits can be achieved as regards the absolute deposition and the durability of silicone deposition on hair. Hydrophilicity is traditionally measured by means of interfacial tension (IFT) which is conventionally established using a pendant drop-type method, as defined hereinbelow. The present inventors also used such a method. The functionalised silicone polymers suitable for use herein accordingly have an IFT of 1 to 12 mN/m, preferably 1 to 10 mN/m, more preferably 1 to 8 mN/m, most preferably from 1 to 4 mN/m.

The present inventors have also established that, for a given functional silicone hydrophilicity level, the silicone fluid viscosity has a profound influence on the level of durability and the tactile sensorial feel of the deposited silicones. Accordingly, the functionalised silicone polymers for use herein have a viscosity in the range 400 to 150,000 mPa.s. More advantageously, the viscosity is in the range 600 to 100,000 mPa.s. More advantageously still, the viscosity is in the range 4000 to 25,000 mPa.s.

Surprisingly, the present inventors have determined that the benefits associated with functionalized silicones having a hydrophilicity and viscosity in the defined ranges apply regardless of chemistry, i.e., regardless of the functional groups concerned.

The conditioning compositions for use herein may comprise from 0.1 to 20 wt %, preferably from 0.25 to 15 wt %, more preferably from 0.5 to 10 wt % and more preferably still from 0.5 to 7.5 wt % of said functionalized silicone polymer.

Functionalized silicone polymers which may be incorporated into compositions according to the invention include organomodified silicones of the pendant or graft type wherein polar functional substituents are incorporated within or onto monovalent organic groups, A1, A2, A3 and A4 used hereinafter, as follows:

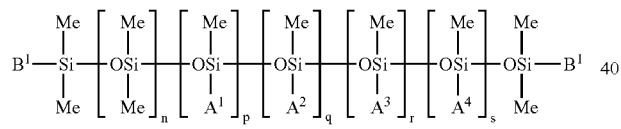

Also included are the organomodified silicones of the block copolymer type wherein these polar functional substituents are incorporated within or onto bivalent organic groups, A1, A2, A3 and A4 used hereinafter.

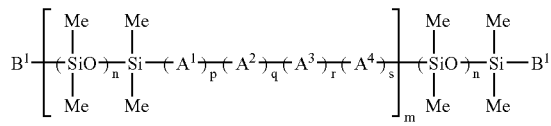

where m is greater than or equal to 1, n is about 50 to 2000, p is about 0 to 50, q is about 0 to 50, is about 0 to 50, s is about 0 to 50, wherein p+q+r+s is greater than or equal to 1, B1 is H, OH, an alkyl or an alkoxy group.

The above functionalized silicones of the pendant or block copolymer type can also incorporate silicone branching groups including MeSiO3/2, known as silsesquioxane or T groups, and SiO4/2, known as Q groups by those skilled in the art.

Organic groups A1, A2, A3 and A4 may be straight, branched or mono- or polycyclic aliphatic, mono or polyunsaturated alkyl, aryl, heteroalkyl, heteroaliphatic or heteroolefinic moiety comprising 3 to 150 carbon atoms together with 0-50 heteroatoms, especially O, N, S, P and can incorporate one or more polar substituents selected from electron withdrawing, electron neutral, or electron donating groups with Hammett sigma para values between −1.0 and +1.5 which can be non-ionic, zwitterionic, cationic or anionic comprising, for example, groups α1, α2, α3, and α4 as defined below; S-linked groups including Sα1, SCN, SO2α1, SO3α1, SSα11, SOα1, SO2Nα1α2, SNα1α2, S(Nα1) α2, S(O)(Nα1) α2, Sα1(Nα2), SONα1α2; O-linked groups including Oα1, OOα1, OCN, ONα1α2; N-linked groups including Nα1α2, Nα1α2α3+, NC, Nα1Oα2, Nα1Sα2, NCO, NCS, NO2, N=Nα1, N=NOα1, Nα1CN, N=C=Nα1, Nα1Nα2α3, Nα1Nα2α3α4, Nα1N=Nα2; other miscellaneous groups including COX, CON3, CONα1α2, CONα1COα2, C(=Nα1)Nα1α2, CHO, CHS, CN, NC, and X.

α1, α2, α3, and α4 may be straight, branched or mono- or polycyclic aliphatic, mono or polyunsaturated alkyl, aryl, heteroalkyl, heteroaliphatic or heteroolefinic moiety comprising 3 to 150 carbon atoms together with 0-50 heteroatoms, especially O, N, S, P.

X is F, Cl, Br, or I.

H is hydrogen, O is oxygen, N is nitrogen, C is carbon, S is sulfur, Cl is chlorine, Br is bromine, I is iodine, F is fluorine.

Hammett sigma para values are discussed in Römpp Chemie Lexikon, Georg Thieme Verlag, Stuttgart, N.Y., 9th Edition, 1995 under "Hammett Gleichung".

Preferred polar functional substituents for use in the present invention as described include, but are not limited to, polyoxyalkylene (polyether), primary and secondary amine, amide, quaternary ammonium, carboxyl, sulfonate, sulfate, carbohydrate, phosphate, and hydroxyl. Other highly preferable polar functional substituents are amine-, polyol- type of the formula

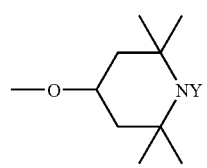

or

wherein each R1 is independently selected from the group consisting of a hydrogen atom and a group of formula —R2NY2, each Y is independently a hydrogen atom or Y', and each Y' is a group of formula

wherein R2 is independently a divalent hydrocarbon group having 1 to 10 carbon atoms, and the proviso that every Y is not H. More preferably, Y1 is a group of the formula —CH2CH(OH)CH2OH and the functionalised silicone is of the pendant type, wherein n is from 200 to 500, p is from 20 to 50 and q, r and s are equal to zero.

More preferably the functional silicones of the present invention include, but are not limited to silicones of the following structure

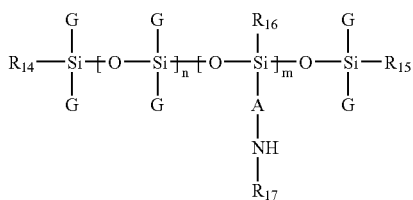

Wherein:

m and n are numbers with a sum (n+m) ranging from 2-2000, n is a number ranging from 1 to 1999, and m is a number ranging from 1 to 1999; and are chosen such that ratio of m:n is 1:1000 to 1:10, preferably 1:1000 to 1:25, more preferably 1:800 to 1:50, most preferably 1:500 to 1:50 and the sum m+n is in the range 150 to 2000, more preferably 250 to 1200, most preferably 300 to 800.

R14, R15, R16, which may be identical or different, are chosen from a hydroxyl radical, C1-C4 alkoxy radicals and methyl.

A is chosen from linear and branched C3-C8 alkenyl radicals.

R17 is chosen from H, phenyl, linear or branched C1-C4 alkyl radical, benzyl or preferably linear or branched (C2-C8) NH2. R4 can also contain amido groups or other hetero atoms.

G is chosen from H, phenyl, hydroxyl, C1-C8 alkyl, preferably methyl.

These aminosilicones may be of the random or block type.

Polymers which are then subsequently reacted with a carbinol compound, preferably glycidol, are also included in the description.

Suitable functionalized silicones of the present invention include, but are not limited to, organomodified silicones with amine functionality available commercially under the trade names such as ADM 100 and ADM1600 from Wacker Silicones, DC2-8211, DC8822, DC8822A, DC8803, DC2-8040, DC2-8813, DC2-8630 and DC8566 from Dow Corning Corporation, KF-862, KF-861, KF-862S, KF-8005, KF-8004, KF-867S, KF-873, and X-52-2328 from Shin-Etsu Corporation, and TSF 4702, TSF 4703, TSF 4704, TSF 4705, TSF 4707, TSF 4708, TSF 4709, F42-B3115, SF 1708, SF 1923, SF 1921, SF 1925, OF TP AC3309, OF 7747, OF-NH TP A13631, OF-NH TP AI3683 from GE Bayer Silicones.

Highly preferred functionalized silicones of the present invention are organomodified silicones with amine functionality with viscosities of greater than 4,000 mPa.s which include, but are not limited to, commercially available fluids under the trade names ADM1100 from Wacker Silicones, DC8803 from Dow Corning Corporation, and TSF 4707 from GE Bayer Silicones.

The functionalized silicones herein can be used together with a durability additive. The durability additive is capable of modifying the functionalized silicones to render them more durable on polar fibrous substrates, especially where the substrate is hair that has been previously damaged through chemical treatments, such as occurs during permanent dyeing, bleaching and permanent waving. The durability additive must be miscible with the functionalized silicone wherein the mixture has a $(Tan\ \delta)^{-1}$ greater than zero, and: Tan $\delta$=G"/G', where G' is the storage modulus and G" is the loss modulus.

Tan $\delta$ describes the ratio of energy lost to energy stored, where Tan $\delta$=G"/G', G" is the loss modulus and G' is the storage modulus. More information on the measurement of dynamic rheological properties can be found in "Rheological Properties of Cosmetics and Toiletries" by Dennis Laba, Cosmetic Science and Technology Series, Volume 13, Marcel Dekker, Inc., ISBN 0-8247-9090-1.

For the avoidance of doubt, $(Tan\ \delta)^{-1}$ is directly equivalent to $1/(Tan\ \delta)$.

Preferably, the durability additive according to the invention comprises one or more organosiloxane resins. Without wishing to be bound by theory, organosiloxane resins are believed to create a 3-dimensional network within the functionalized silicone fluid giving rise to vicoelasticity thereby improving the adhesive properties of the fluid and hence the durability on a fibrous substrate. Preferably, the organosiloxane resin is insoluble in water.

Organosiloxane resins which my be included in the durability additive according to the invention comprise combinations of $R_3SiO_{1/2}$ "M" units, $R_2SiO$ "D" units, $RsiO_{3/2}$ "T" units, $SiO_2$ "Q" units in ratios to each other that satisfy the relationship $R_nSiO_{(4-n)/2}$ where n is a value between 1.0 and 1.50 and R is chosen from C1-C4 lower alkyl radicals such as methyl and a phenyl radical. Silanol or alkoxy functionalities may also be present in the resin structure.

More preferably, the organosiloxane resins comprise repeating monofunctional $R_3SiO_{1/2}$ "M" units and the quadrafunctional $SiO_2$ "Q" units, otherwise known as "MQ" resins. In this case, the ratio of the "M" to "Q" functional units is advantageously from 0.7 and the value of n is 1.2. Organosiloxane resins such as these are commercially available as SR1000 available from GE Bayer Silicones and Wacker 803 from Wacker Silicones.

Advantageously, the organosiloxane resins according to the invention are solid at about 25° C. and have a molecular weight range of from 1,000 to 10,000 grams/mole.

The conditioning composition according to the present invention may include a cosmetically acceptable vehicle to act as a diluent, dispersant, or carrier for the silicone oil in the composition, so as to facilitate the distribution of the silicone oil when the composition is applied. The vehicle may be an aqueous emulsion, water, liquid or solid emollients, solvents, humectants, propellants, thickeners and powders.

Advantageously, the conditioning compositions according to the present invention may be in the form of an emulsion with water as a primary component, although aqueous organic solvents, such as those listed above, may also be included. The emulsion may be a water-in-oil emulsion, an oil-in-water emulsion, a water-in-oil-in-water multiple emulsion, or an oil-in-water-in-oil multiple emulsion, but is preferably an oil-in-water emulsion (a silicone-in-water emulsion). In such a case the functionalized silicone particle size is preferably greater than 500 nm, more preferably greater than 1 μm and even more preferably greater than 2 μm.

The aqueous continuous phase of the emulsion may further comprise an emulsifier to facilitate the formation of the emulsion. Emulsifiers for use in the aqueous continuous phase of the emulsion may include an anionic surfactant, cationic surfactant, amphoteric surfactant, water-soluble polymeric surfactant, water-soluble silicone-containing surfactant, nonionic surfactant having an HLB of greater than about 10, or a surfactant system capable of forming stabilizing liquid crystals around the silicone droplets. The nonionic surfactant preferably has an HLB of at least 12, and more preferably, an HLB value of at least about 15. Surfactants belonging to these classes are listed in McCutcheon's Emulsifiers and Detergents, North American and International Editions, MC Publishing Co., Glen Rock N.J., pages 235-246(1993).

The emulsifier for the aqueous phase does not gel the aqueous phase. The emulsifier however may be capable of forming a stabilizing layer of lamellar liquid crystals around silicone droplets. For conciseness, the term "liquid crystal structure" as used herein, should be taken to also include gel networks, which are solidified liquid crystals. The surfactant system can be a single surfactant or a blend of surfactants. In some cases, a particular surfactant cannot form a liquid crystal structure alone, but can participate in the formation of liquid crystals in the presence of a second surfactant. Exemplary classes of surfactants capable of participating in the formation of a liquid crystal, but are not limited to specific cationic surfactants, anionic surfactants, nonionic surfactants, quaternary ammonium surfactants and lipid surfactants.

Preferred non-ionic surfactants for the formation of liquid crystals in the aqueous continuous phase are of the nonionic type and include C16-20 fatty alcohols, and C16-20 fatty alcohol ethoxylates with 1 to 30 ethylene oxide groups. Specific examples include cetearyl alcohol, cetyl alcohol, stearyl alcohol, arachidyl alcohol, oleyl alcohol, ceteareth ethoxylates with between 10 and 30 ethylene oxide groups, ceteth ethoxylates with between 10 to 30 ethylene oxide groups, steareth ethoxylates with between 10 and 30 ethoxylates, and combinations thereof. Preferably, C16-22 fatty alcohols are used in combination with C16-22 fatty alchol ethoxylates at a ratio of between 10:1 to 0.5:1, more preferably between 6:1 and 1:1, and most preferably between 5:1 and 1.5:1.

Preferred cationic surfactants contain quaternary ammonium compounds of formula: [R18R19R20R21N]+X-, where R18 is an alkyl or alkenyl group having from about 8 to 22 carbon atoms, R19 and R20 are both independently either an alkyl or alkenyl group having from about 8 to 22 carbon atoms or alkyl or hydroxyalkyl group having from about 1 to 4 carbon atoms, R21 is an alkyl or hydroxyalkyl group having from about 1 to 4 carbon atoms, and X- is a salt forming anion (e.g. chloride, bromide, acetate, alkylsulfate).

Advantageously, in order to facilitate formation of liquid crystals, the surfactant system may also comprise amidoamines of the following general formula: R22CONH(CH2)m N(R23)2, wherein R22 is a residue of C8 to C24 fatty acids, R23 is a C1 to C4 alkyl, and m is an integer from 1 to 4. Preferred amidoamine useful in the present invention includes stearamidopropyldimethylamine, stearamidopropyldiethylamine, stearamidoethyl-diethylamine, stearamidoethyldimethylamine, palmitamidopropyldimethylamine, paimit-amidopropyldiethylamine, palmitamidoethyldiethylamine, palmitamido-ethyldimethylamine, behenamidopropyldimethylamine, behenamidopropyldiethylamine, behenamidoethyldiethylamine, behenamidoethyldimethylamine, arachidamido-propyldimethylamine, arachidamido-propyldiethylamine, arachidamidoethyldiethylamine, arachidamidoethyldimethylamine, and mixtures thereof, more preferably stearamido-propyldimethylamine, stearamidoethyldiethylamine, and mixtures thereof.

More advantageously, the amidoamines are partially quaternized with the acids selected from the group consisting of L-glutamic acid, lactic acid, hydrochloric acid, malic acid, succinic acid, acetic acid, fumaric acid, L-glutamicio acid hydrochloride, tartaric acid, and mixtures thereof; preferably L-glutamic acid, lactic acid, hydrochloric acid, and mixtures thereof. Preferably, the mole ratio of amidoamine to acid is from about 1:0.3 to about 1:1, more preferably from about 1:0.5 to about 1:0.

The aqueous continuous phase should ideally comprise the emulsifier in an amount sufficient to stabilize the silicone. In one embodiment, the aqueous continuous phase comprises the emulsifier in an amount of from about 0.1% to about 15%, and more preferably from about 0.1% to about 10%, based on the weight of the aqueous continuous phase.

The conditioning composition of the present invention may include optional benefit materials and cosmetic adjuncts, as long as the benefit materials or the adjuncts do not eliminate or substantially reduce the performance or shelf stability of the composition. The additional ingredients may include, for example dyes and coloring agents, fragrances; anionic, cationic, non-ionic, amphoteric or zwitterionic surfactants; buffers, masking fragrances, dispersing agents, stabilizers, cationic polymers, perfumes, non-ionic polymers, anionic polymers, complex coacervates, complex coacervate capsules, metal salts, lewis acids, buffering agents, particulate thickeners, polymeric thickeners, wax thickeners, oils, emollients, humectants, moisturizers, pearlescents, opacifiers, enzymes, suspending agents, antimicrobials, preservatives, proteins, herb and plant extracts, bleach, peroxide, polyols, silicones, antibodies, pH adjusting agents including pH buffers, viscosity modifiers, preservatives, viscosity enhancers, gelling agents, chelators, oxidising agents, reducing agents, UV filters, emulsifying agents, antioxidants, moisturizing and conditioning agents, and other common adjuvants well known to those skilled in the art.

In one embodiment, a stabilizer comprising a polymeric thickener is employed. When polymeric thickeners are employed as the stabilizer in the emulsion treatment compositions herein, they are typically included in an amount ranging from about 0.01% to about 5%, preferably from about 0.3% to about 3%, based on the weight of the aqueous phase. The polymeric thickener is preferably an anionic, nonionic, cationic or hydrophobically modified polymer of natural, modified natural or synthetic origin from plants, microbials, animals or petroleum raw materials. Those skilled in the art would be able to choose either one or a selection of polymeric thickeners to stabilize the emulsion composition. Alternatively, the stabilizer employed can comprise C10-C22 ethylene glycol fatty acid esters. C10-C22 ethylene glycol fatty acid esters can also desirably be employed in combination with the polymeric thickeners hereinbefore described. The ester is preferably a diester, more preferably a C14-C18 diester, most preferably ethylene glycol distearate. When C10-C22 ethylene glycol fatty acid esters are utilized as the stabilizer in the emulsion treatment compositions herein, they are typically present in an amount of from about 3% to about 10%, preferably from about 5% to about 8%, more preferably from about 6% to about 8%, based on the weight of the aqueous phase.

For use, the conditioning compositions according to an embodiment of the invention may be provided at a pH from about 3 to 11, preferably from 4 to 10.5.

The conditioning compositions according to the present invention may be provided in any suitable physical form, for example as low to moderate to high viscosity liquids, lotions, milks, mousses, dispersions, sprays, gels, foams, aerosols, and creams. These compositions may be produced by procedures well known to the skilled artisan.

The conditioning compositions of the present invention can be formulated as a fluid, lotion, fluid cream or cream having a viscosity from 500 to 100,000 mPa.s or above. The compositions can be packaged in a suitable container to suit its viscosity and intended use by the consumer. For example, a lotion or fluid cream can be packaged in a bottle, a roll-ball applicator, a propellant-driven aerosol device, a container fitted with a pump suitable for hand or finger operation, or the like. When the composition is a cream, it can simply be stored in a non-deformable bottle or squeeze container, such as a tube or a lidded jar.

Test Methods

Interfacial Tension Measurement Protocol:

The silicone/water interfacial tensions of the organomodified silicones were measured via pendant drop shape analysis on a Kruss DSA-10 instrument as taught in F. K. Hansen, G. Rodsrun, "Surface tension by pendant drop. A fast standard instrument using computer image analysis", Journal of Colloid and Interface Science, Volume 141, Issue 1, January 1991, pages 1-9. The accuracy of this method is dependent upon the density difference between the reference fluid (usually water) and the test fluid. Given that many of the present functionalized silicones have densities approaching that of water, D2O (with a density of 1.1 g/cm-3) was substituted for H2O as the more dense phase, in order to ensure a sufficient density difference. The respective densities of the organo-modified silicones were measured with a Calculating Precision Density Meter DMA 55 instrument from Apollo Scientific Limited.

Viscosity of Functionalized Silicone Fluids—Measurement Protocol

An AR 500 rotational rheometer (TA Instruments Ltd., Leatherhead, Surrey KT22 7UQ, UK) is used to determine the viscosity of the functionalized silicone fluids used herein. The determination is performed at 30° C., with the 4 cm 2° steel cone measuring system set with a 49 μm (micron) gap and is performed via the programmed application of a shear stress of 0.5 to 590 Pa over a 2 minute time period. These data are used to create a shear rate vs. shear stress curve for the material. This flow curve can then be modelled in order to provide a material's viscosity. These results were fitted with the following well-accepted Newtonian model: Viscosity, $\mu=\sigma/\gamma$ (where $\sigma$ is shear stress; $\gamma$ is shear rate)

The following examples illustrate the present invention.

EXAMPLES

Examples 1-4 are Conditioning Compositions

| | #1 | #2 | #3 | #4 |
|---|---|---|---|---|
| Demineralised water | qs to 100 | qs to 100 | qs to 100 | qs to 100 |
| Cetyl alcohol | 2.3 | 2.3 | 4.0 | 4.0 |
| Stearyl alcohol | 2.3 | 2.3 | 2.0 | 2.0 |
| Ceteareth-25 | 1.5 | 1.5 | — | — |
| Phonoxyethanol | 0.1 | 0.1 | 0.3 | 0.3 |
| Sodium benzoate | 0.1 | 0.1 | — | — |
| Tetrasodium EDTA (87%) | 0.1 | 0.1 | 0.1 | 0.1 |
| Stearamidopropyl-dimethyamine | — | — | 1.6 | 2.0 |
| L-Glutamic acid | — | — | 0.5 | 0.7 |
| Dicetyldimonium chloride | — | — | 0.5 | — |
| Benzyl alcohol | — | — | 0.3 | — |
| (Silicone Premix) | (5.000) | (5.000) | (3.000) | (7.000) |
| Aminofunction silicone sold under the name Wacker Belsil ADM1100 by the company Wacker Chemie | 4.995 | — | — | 7.000 |
| Aminofunctional silicone sold under the name TSF4707 by GE Bayer Silicone | — | 5.000 | 2.995 | — |
| MQ resin sold under the name SR1000 by the company GE Bayer Silicones | 0.005 | — | 0.005 | — |

Examples 5-8 are Coloring Compositions

In these examples, compositions 5 to 8 are coloring compositions, also referred to as dye carriers, comprising the dye and the cationic polymer. Prior to use, 30 grams of dye carrier and 30 grams of oxidizing system were mixed together so as to form a composition comprising an oxidising agent and a cationic polymer. This mixture was then applied to a hair swatch. After leaving the composition to act for 30 minutes, the swatch was thoroughly rinsed with water, the conditioner was then applied to the hair and rinsed before the hair was then dried. The hair treated with the compositions had long lasting conditioned feel.

| | #5 | #6 | #7 | #8 |
|---|---|---|---|---|
| Dye carrier: | | | | |
| Water | qs to 100% | qs to 100% | qs to 100% | qs to 100% |
| Steareth-21 | 3 | 3 | 3 | 3 |
| Cocamide MEA | 4 | 4 | 4 | 4 |
| Sodium sulfite | 0.1 | 0.1 | 0.1 | 0.1 |
| EDTA | 0.1 | 0.1 | 0.1 | 0.1 |
| Erythorbic acid | 0.4 | 0.4 | 0.4 | 0.4 |
| P-phenylenediamine | 0.3 | 0.3 | 0.3 | 0.3 |
| P-aminophenol | 0.2 | 0.2 | 0.2 | 0.2 |
| 2-methylresorcinol | 0.5 | 0.5 | 0.5 | 0.5 |
| 4-amino-2-hydroxytoluene | 0.2 | 0.2 | 0.2 | 0.2 |
| Sodium sulphate | 1 | 1 | 1 | 1 |
| C12–15 Pareth-3 | 9 | 9 | 9 | 9 |
| Dilinoleic acid | 2 | 2 | 2 | 2 |
| Fragrance | 1 | 1 | 1 | 1 |
| Ammonium hydroxide | 7.5 | 7.5 | 7.5 | 7.5 |
| Sodium metasilicate | 0.2 | 0.2 | 0.2 | 0.2 |
| Behentrimonium chloride | 3 | 3 | 3 | 3 |
| Oleth-10 | 5 | 5 | 5 | 5 |
| Linoleamidopropyl dimethylamine dimmer dilinoleate | 4 | 4 | 4 | 4 |
| Polyquaternium-22 | 1 | 0.5 | 1 | 0 |
| Oxidizing component: | | | | |
| Water | qs to 100% | qs to 100% | qs to 100% | qs to 100% |
| Hydrogen peroxide (35% active) | 17.5 | 17.5 | 17.5 | 17.5 |
| Laureth-23 | 0.5 | 0.5 | 0.5 | 0.5 |
| Etidronic acid | 0.01 | 0.01 | 0.01 | 0.01 |
| Cetearyl alcohol and ceteareth-20 | 2.0 | 2.0 | 2.0 | 2.0 |
| Styrene/PVP copolymer | 0.5 | 0.5 | 0.5 | 0.5 |
| Steareth-21 | 0.5 | 0.5 | 0.5 | 0.5 |
| Polyquaternium-37 | 0 | 0 | 0.5 | 0.5 |
| Polyquaternium-22 | 0 | 0.5 | 0 | 1 |

Examples 9-12 are Bleaching Compositions

In these examples, compositions 9 to 12 are an alkalising system which comprise the cationic polymer. Prior to use, 30 grams of the alkalising system, 60 grams of oxidizing system and 15 grams of activating powders were mixed together to form a bleaching composition. This bleaching composition was then applied to a hair swatch. After leaving the composition to act for 30 minutes, the swatch was thoroughly rinsed with water, the conditioner was then applied to the hair and rinsed before the hair was then dried. The hair treated with the compositions had long lasting conditioned feel.

|  | #9 | #10 | #11 | #12 |
|---|---|---|---|---|
| Alkalising system: | | | | |
| Water | qs to 100% | qs to 100% | qs to 100% | qs to 100% |
| Steareth-21 | 3 | 3 | 3 | 3 |
| Cocamide MEA | 4 | 4 | 4 | 4 |
| Sodium sulfite | 0.1 | 0.1 | 0.1 | 0.1 |
| EDTA | 0.1 | 0.1 | 0.1 | 0.1 |
| Erythorbic acid | 0.4 | 0.4 | 0.4 | 0.4 |
| Sodium sulphate | 1 | 1 | 1 | 1 |
| C12–15 Pareth-3 | 9 | 9 | 9 | 9 |
| Dilinoleic acid | 2 | 2 | 2 | 2 |
| Fragrance | 1 | 1 | 1 | 1 |
| Ammonium hydroxide | 7.5 | 7.5 | 7.5 | 7.5 |
| Sodium metasilicate | 0.2 | 0.2 | 0.2 | 0.2 |
| Behentrimonium chloride | 3 | 3 | 3 | 3 |
| Oleth-10 | 5 | 5 | 5 | 5 |
| Linoleamidopropyl dimethylamine dimmer dilinoleate | 4 | 4 | 4 | 4 |
| Polyquaternium-22 | 1 | 0.5 | 1 | 0 |
| Oxidizing component: | | | | |
| Water | qs to 100% | qs to 100% | qs to 100% | qs to 100% |
| Hydrogen peroxide (35% active) | 17.5 | 17.5 | 17.5 | 17.5 |
| Laureth-23 | 0.5 | 0.5 | 0.5 | 0.5 |
| Etidronic acid | 0.01 | 0.01 | 0.01 | 0.01 |
| Cetearyl alcohol and ceteareth-20 | 2.0 | 2.0 | 2.0 | 2.0 |
| Styrene/PVP copolymer | 0.5 | 0.5 | 0.5 | 0.5 |
| Steareth-21 | 0.5 | 0.5 | 0.5 | 0.5 |
| Polyquaternium-37 | 0 | 0 | 0.5 | 0.5 |
| Polyquaternium-22 | 0 | 0.5 | 0 | 1 |
| Activating powder | | | | |
| Potassium persulfate | 40 | 40 | 40 | 40 |
| Ammonium persulfate | 20 | 20 | 20 | 20 |
| Sodium Silicate | 36 | 36 | 36 | 36 |
| Silica | 2 | 2 | 2 | 2 |
| Sodium Lauryl sulphate | 1 | 1 | 1 | 1 |
| Disodium EDTA | 1 | 1 | 1 | 1 |

Examples 13-16 are Permanently Reshaping Compositions

In these examples, compositions 13-16 are reducing compositions which comprise the cationic polymer. The reducing composition was applied to a hair swatch, rolled up beforehand on a curler of 9 mm diameter. After leaving the composition to act for ten minutes, the swatch was rinsed thoroughly with water. The oxidising composition was then applied to the hair. After leaving the composition to act for ten minutes, the swatch was again rinsed thoroughly with water. The hair was then unrolled from the roller, the conditioner was then applied to the hair and rinsed before the hair was then dried. The hair treated with the compositions had long lasting conditioned feel.

|  | #13 | #14 | #15 | #16 |
|---|---|---|---|---|
| Reducing component: | | | | |
| Demineralised water | qs to 100 | qs to 100 | qs to 100 | qs to 100 |
| Thioglycolic acid | 9.2 | 9.2 | 9.2 | 9.2 |
| Ammonium hydroxide | To pH 9.3 | To pH 9.3 | To pH 9.3 | To pH 9.3 |
| Cetearyl alcohol and ceteareth-20 | 3.0 | 3.0 | 3.0 | 3.0 |
| EDTA | 0.4 | 0.4 | 0.4 | 0.4 |
| Fragrance | 0.4 | 0.4 | 0.4 | 0.4 |
| Polyquaternium-22 | 1 | 0.5 | 1 | 0 |
| Oxidizing component: | | | | |
| Demineralised water | qs to 100% | qs to 100% | qs to 100% | qs to 100% |
| Aqueous hydrogen peroxide (35% in water) | 17.5 | 17.5 | 17.5 | 17.5 |
| Laureth-23 | 0.5 | 0.5 | 0.5 | 0.5 |
| Etidronic acid | 0.01 | 0.01 | 0.01 | 0.01 |
| Cetearyl alcohol and ceteareth-20 | 2.0 | 2.0 | 2.0 | 2.0 |
| Styrene/PVP copolymer | 0.5 | 0.5 | 0.5 | 0.5 |
| Steareth-21 | 0.5 | 0.5 | 0.5 | 0.5 |
| Polyquaternium-37 | 0 | 0 | 0.5 | 0.5 |
| Polyquaternium-22 | 0 | 0.5 | 0 | 1 |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A kit-of-parts for the treatment of hair which comprises:
   a) a composition comprising an oxidising agent,
   b) a composition comprising a cationic polymer, to be used in a step where said hair is oxidised, and
   c) a conditioning composition to be used in a conditioning step subsequent to said oxidizing step, said conditioning composition comprising a functionalized silicone comprising at least one amino functional group, said functionalized silicone with an interfacial tension (IFT) between about 1 and about 12 mN/m and a viscosity from about 400 to about 150,000 cps,
   wherein said functionalized silicone deposits durably onto hair and
   wherein said functionalized silicone is

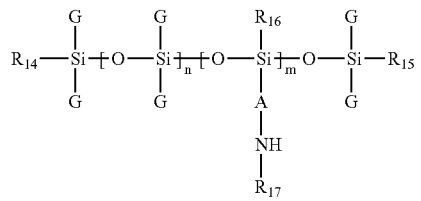

wherein:

m and n are numbers with a sum (n+m) ranging from about 2 to about 2000, n is a number ranging from about 1 to about 1999, and m is a number ranging from about 1 to about 1999; and are chosen such that ratio of m:n is about 1:1000 to about 1:10 and the sum m+n is in the range of about 150 to about 2000;

R14, R15, R16, which may be identical or different, are selected from the group consisting of a hydroxyl radical, C1-C4 alkoxy radicals and methyl;

A is selected from the group consisting of linear and branched C3-C8 alkenyl radicals;

R17 is selected from the group consisting of H, phenyl, linear and branched C1-C4 alkyl radicals, linear and branched (C2-C8)NH2, and benzyl; R14 can also contain amido groups or other hetero atoms;

G is selected from the group consisting of H, phenyl, hydroxyl and C1-C8 alkyl; and said aminosilicones can be of the random or block type.

2. A kit-of-parts according to claim 1, wherein said functionalized silicone is

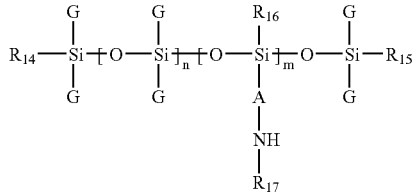

wherein m and n are numbers with a sum (n+m) ranging from about 2 to about 2000, n is a number ranging from about 1 to about 1999, and m is a number ranging from about 1 to about 1999; and are chosen such that ratio of m:n is about 1:1000 to about 1:10 and the sum m+n is in the range of about 150 to about 2000; R14, R15, R16, which may be identical or different, are selected from the group consisting of a hydroxyl radical, C1-C4 alkoxy radicals and methyl; A is selected from the group consisting of linear and branched C3-C8 alkenyl radicals; R17 is selected from the group consisting of linear and branched (C2-C8)NH2; R14 can also contain amido groups or other hetero atoms; G is methyl; and said aminosilicones can be of the random or block type.

* * * * *